United States Patent
Young et al.

(10) Patent No.: US 9,504,416 B2
(45) Date of Patent: Nov. 29, 2016

(54) SMART SEAT MONITORING SYSTEM

(71) Applicant: SleepIQ Labs Inc., San Jose, CA (US)

(72) Inventors: Steven J. Young, Los Gatos, CA (US); Carl Hewitt, San Jose, CA (US); Al Luckow, Ben Lomond, CA (US)

(73) Assignee: SleepIQ Labs Inc., San Jose, CA (US)

( * ) Notice: Subject to any disclaimer, the term of this patent is extended or adjusted under 35 U.S.C. 154(b) by 0 days.

(21) Appl. No.: 14/323,195

(22) Filed: Jul. 3, 2014

(65) Prior Publication Data

US 2015/0008710 A1 Jan. 8, 2015

Related U.S. Application Data

(60) Provisional application No. 61/842,465, filed on Jul. 3, 2013.

(51) Int. Cl.

| | |
|---|---|
| *A47C 7/02* | (2006.01) |
| *A61B 5/18* | (2006.01) |
| *B60N 2/00* | (2006.01) |
| *A47C 27/08* | (2006.01) |
| *A47C 31/12* | (2006.01) |
| *B60N 2/02* | (2006.01) |
| *B60N 2/44* | (2006.01) |
| *A61B 5/00* | (2006.01) |
| *A61B 5/0205* | (2006.01) |
| *A61B 5/11* | (2006.01) |

(52) U.S. Cl.
CPC ............... *A61B 5/18* (2013.01); *A47C 27/083* (2013.01); *A47C 31/126* (2013.01); *B60N 2/002* (2013.01); *B60N 2/0276* (2013.01); *B60N 2/448* (2013.01); *B60N 2/4415* (2013.01); *A61B 5/0205* (2013.01); *A61B 5/1118* (2013.01); *A61B 5/4809* (2013.01); *A61B 5/6893* (2013.01); *B60N 2002/4485* (2013.01)

(58) Field of Classification Search
CPC .................................................. B60N 2002/4485
USPC .......... 297/284.1, 284.2, 284.3, 217.1, 217.2
See application file for complete search history.

(56) References Cited

U.S. PATENT DOCUMENTS

| | | |
|---|---|---|
| 3,727,606 A | 4/1973 | Sielaff |
| 4,146,885 A | 3/1979 | Lawson, Jr. |
| 4,299,233 A | 11/1981 | Lemelson |
| 4,438,771 A | 3/1984 | Friesen et al. |

(Continued)

OTHER PUBLICATIONS

U.S. Appl. No. 14/146,281, filed Jan. 2, 2014, Palashewski et al.

(Continued)

*Primary Examiner* — Laurie K Cranmer
(74) *Attorney, Agent, or Firm* — Fish & Richardson P.C.

(57) ABSTRACT

A seat monitoring system comprises a first layer of one or more fluid bladders packaged within a seat, a pump in fluid communication with the first layer, the pump operable to increase fluid pressure of each bladder within the first layer, an array of one or more sensors in fluid communication with the first layer and operative to sense pressure and pressure changes within each bladder within the first layer and a controller configured to: collect pressure data; determine from the pressure data a monitored parameter relevant to a subject in the seat; and change an aspect of the seat based on the monitored parameter. Methods of using the seat monitoring system can include determining a drowsiness threshold and altering a user that he or she is getting drowsy.

17 Claims, 5 Drawing Sheets

(56) References Cited

U.S. PATENT DOCUMENTS

| | | |
|---|---|---|
| 4,657,026 A | 4/1987 | Tagg |
| 4,662,012 A | 5/1987 | Tarbet |
| 4,766,628 A | 8/1988 | Walker |
| 4,788,729 A | 12/1988 | Walker |
| 4,829,616 A | 5/1989 | Walker |
| 4,890,344 A | 1/1990 | Walker |
| 4,897,890 A | 2/1990 | Walker |
| 4,908,895 A | 3/1990 | Walker |
| 4,991,244 A | 2/1991 | Walker |
| 5,062,169 A | 11/1991 | Kennedy et al. |
| 5,144,706 A | 9/1992 | Walker et al. |
| 5,170,522 A | 12/1992 | Walker |
| 5,197,490 A | 3/1993 | Steiner et al. |
| 5,459,452 A | 10/1995 | DePonte |
| 5,509,154 A | 4/1996 | Shafer et al. |
| 5,515,865 A | 5/1996 | Scanlon |
| 5,564,140 A | 10/1996 | Shoenhair et al. |
| 5,642,546 A | 7/1997 | Shoenhair |
| 5,652,484 A | 7/1997 | Shafer et al. |
| 5,675,855 A | 10/1997 | Culp |
| 5,684,460 A | 11/1997 | Scanlon |
| 5,699,038 A | 12/1997 | Ulrich et al. |
| 5,724,990 A | 3/1998 | Ogino |
| 5,765,246 A | 6/1998 | Shoenhair |
| 5,771,511 A | 6/1998 | Kummer et al. |
| 5,796,340 A | 8/1998 | Miller |
| 5,844,488 A | 12/1998 | Musick |
| 5,848,450 A | 12/1998 | Oexman et al. |
| 5,903,941 A | 5/1999 | Shafer et al. |
| 5,904,172 A | 5/1999 | Gifft et al. |
| 5,948,303 A | 9/1999 | Larson |
| 5,964,720 A | 10/1999 | Pelz |
| 5,989,193 A | 11/1999 | Sullivan |
| 6,024,699 A | 2/2000 | Surwit et al. |
| 6,037,723 A | 3/2000 | Shafer et al. |
| 6,058,537 A | 5/2000 | Larson |
| 6,062,216 A | 5/2000 | Corn |
| 6,108,844 A | 8/2000 | Kraft et al. |
| 6,120,441 A | 9/2000 | Griebel |
| 6,146,332 A | 11/2000 | Pinsonneault et al. |
| 6,147,592 A | 11/2000 | Ulrich et al. |
| 6,161,231 A | 12/2000 | Kraft et al. |
| 6,202,239 B1 | 3/2001 | Ward et al. |
| 6,208,250 B1 | 3/2001 | Dixon et al. |
| 6,234,642 B1 | 5/2001 | Bokaemper |
| 6,272,378 B1 | 8/2001 | Baumgart-Schmitt |
| 6,386,201 B1 | 5/2002 | Fard |
| 6,396,224 B1 | 5/2002 | Luff et al. |
| 6,397,419 B1 | 6/2002 | Mechache |
| 6,438,776 B2 | 8/2002 | Ferrand et al. |
| 6,450,957 B1 | 9/2002 | Yoshimi et al. |
| 6,468,234 B1 | 10/2002 | Ford et al. |
| 6,483,264 B1 | 11/2002 | Shafer et al. |
| 6,485,441 B2 | 11/2002 | Woodward |
| 6,546,580 B2 | 4/2003 | Shimada |
| 6,547,743 B2 | 4/2003 | Brydon |
| 6,561,047 B1 | 5/2003 | Gladney |
| 6,566,833 B2 | 5/2003 | Bartlett |
| 6,661,345 B1 * | 12/2003 | Bevan ............... G08B 21/06 340/575 |
| 6,686,711 B2 | 2/2004 | Rose et al. |
| 6,708,357 B2 | 3/2004 | Gaboury et al. |
| 6,719,708 B1 | 4/2004 | Jansen |
| 6,763,541 B2 | 7/2004 | Mahoney et al. |
| 6,778,090 B2 | 8/2004 | Newham |
| 6,804,848 B1 | 10/2004 | Rose |
| 6,832,397 B2 | 12/2004 | Gaboury et al. |
| 6,840,117 B2 | 1/2005 | Hubbard, Jr. |
| 6,840,907 B1 | 1/2005 | Brydon |
| 6,847,301 B1 | 1/2005 | Olson |
| 6,878,121 B2 | 4/2005 | Krausman |
| 6,883,191 B2 | 4/2005 | Gaboury et al. |
| 6,993,380 B1 | 1/2006 | Modarres |
| 7,041,049 B1 | 5/2006 | Raniere |
| 7,077,810 B2 | 7/2006 | Lange et al. |
| 7,150,718 B2 | 12/2006 | Okada |
| 7,237,287 B2 | 7/2007 | Weismiller et al. |
| 7,253,366 B2 | 8/2007 | Bhai |
| 7,304,580 B2 | 12/2007 | Sullivan et al. |
| 7,314,451 B2 | 1/2008 | Halperin et al. |
| 7,321,811 B1 | 1/2008 | Rawls-Meehan |
| 7,330,127 B2 | 2/2008 | Price et al. |
| 7,389,554 B1 | 6/2008 | Rose |
| 7,396,331 B2 | 7/2008 | Mack |
| 7,429,247 B2 | 9/2008 | Okada et al. |
| 7,437,787 B2 | 10/2008 | Bhai |
| 7,465,280 B2 | 12/2008 | Rawls-Meehan |
| 7,480,951 B2 | 1/2009 | Weismiller |
| 7,506,390 B2 | 3/2009 | Dixon et al. |
| 7,520,006 B2 | 4/2009 | Menkedick et al. |
| 7,524,279 B2 | 4/2009 | Auphan |
| 7,532,934 B2 | 5/2009 | Lee et al. |
| 7,538,659 B2 | 5/2009 | Ulrich |
| 7,568,246 B2 | 8/2009 | Weismiller et al. |
| 7,637,859 B2 | 12/2009 | Lindback et al. |
| 7,652,581 B2 | 1/2010 | Gentry et al. |
| 7,666,151 B2 | 2/2010 | Sullivan et al. |
| 7,669,263 B2 | 3/2010 | Menkedick et al. |
| 7,676,872 B2 | 3/2010 | Block et al. |
| 7,685,663 B2 | 3/2010 | Rawls-Meehan |
| 7,699,784 B2 | 4/2010 | Wan et al. |
| 7,717,848 B2 | 5/2010 | Heruth et al. |
| 7,735,918 B2 * | 6/2010 | Beck ............... A47C 1/0242 297/217.3 |
| 7,749,154 B2 | 7/2010 | Cornel |
| 7,784,128 B2 | 8/2010 | Kramer |
| 7,785,257 B2 | 8/2010 | Mack et al. |
| 7,805,785 B2 | 10/2010 | Rawls-Meehan |
| 7,841,031 B2 | 11/2010 | Rawls-Meehan |
| 7,849,545 B2 | 12/2010 | Flocard et al. |
| 7,854,031 B2 | 12/2010 | Rawls-Meehan |
| 7,860,723 B2 | 12/2010 | Rawls-Meehan |
| 7,862,523 B2 | 1/2011 | Ruotoistenmaki |
| 7,865,988 B2 | 1/2011 | Koughan et al. |
| 7,868,757 B2 | 1/2011 | Radivojevic et al. |
| 7,869,903 B2 | 1/2011 | Turner et al. |
| 7,930,783 B2 | 4/2011 | Rawls-Meehan |
| 7,933,669 B2 | 4/2011 | Rawls-Meehan |
| 7,953,613 B2 | 5/2011 | Gizewski |
| 7,954,189 B2 | 6/2011 | Rawls-Meehan |
| 7,956,755 B2 | 6/2011 | Lee et al. |
| 7,967,739 B2 | 6/2011 | Auphan |
| 7,979,169 B2 | 7/2011 | Rawls-Meehan |
| 8,019,486 B2 | 9/2011 | Rawls-Meehan |
| 8,020,230 B2 | 9/2011 | Rawls-Meehan |
| 8,028,363 B2 | 10/2011 | Rawls-Meehan |
| 8,032,263 B2 | 10/2011 | Rawls-Meehan |
| 8,032,960 B2 | 10/2011 | Rawls-Meehan |
| 8,046,114 B2 | 10/2011 | Rawls-Meehan |
| 8,046,115 B2 | 10/2011 | Rawls-Meehan |
| 8,046,116 B2 | 10/2011 | Rawls-Meehan |
| 8,046,117 B2 | 10/2011 | Rawls-Meehan |
| 8,050,805 B2 | 11/2011 | Rawls-Meehan |
| 8,052,612 B2 | 11/2011 | Tang |
| 8,065,764 B2 | 11/2011 | Kramer |
| 8,069,852 B2 | 12/2011 | Burton |
| 8,073,535 B2 | 12/2011 | Jung et al. |
| 8,078,269 B2 | 12/2011 | Suzuki et al. |
| 8,078,336 B2 | 12/2011 | Rawls-Meehan |
| 8,078,337 B2 | 12/2011 | Rawls-Meehan |
| 8,083,682 B2 | 12/2011 | Dalal et al. |
| 8,090,478 B2 | 1/2012 | Skinner et al. |
| 8,092,399 B2 | 1/2012 | Sasaki |
| 8,094,013 B1 | 1/2012 | Lee et al. |
| 8,096,960 B2 | 1/2012 | Loree et al. |
| 8,146,191 B2 | 4/2012 | Bobey et al. |
| 8,150,562 B2 | 4/2012 | Rawls-Meehan |
| 8,166,589 B2 | 5/2012 | Hijlkema |
| 8,181,296 B2 | 5/2012 | Rawls-Meehan |
| 8,211,014 B2 * | 7/2012 | David ............... A61B 5/0205 128/897 |
| 8,266,742 B2 | 9/2012 | Andrienko |
| 8,272,892 B2 | 9/2012 | McNeely et al. |
| 8,276,585 B2 | 10/2012 | Buckley |

(56) References Cited

U.S. PATENT DOCUMENTS

| | | | |
|---|---|---|---|
| 8,279,057 B2 | 10/2012 | Hirose | |
| 8,280,748 B2 | 10/2012 | Allen | |
| 8,281,433 B2 | 10/2012 | Riley et al. | |
| 8,282,452 B2 | 10/2012 | Grigsby et al. | |
| 8,284,047 B2 | 10/2012 | Collins, Jr. | |
| 8,287,452 B2 | 10/2012 | Young et al. | |
| 8,336,369 B2 | 12/2012 | Mahoney | |
| 8,341,784 B2 | 1/2013 | Scott | |
| 8,341,786 B2 | 1/2013 | Oexman et al. | |
| 8,348,840 B2 | 1/2013 | Heit et al. | |
| 8,350,709 B2 | 1/2013 | Receveur | |
| 8,375,488 B2 | 2/2013 | Rawls-Meehan | |
| 8,376,954 B2 | 2/2013 | Lange et al. | |
| 8,382,484 B2 | 2/2013 | Wetmore et al. | |
| 8,386,008 B2 | 2/2013 | Yuen et al. | |
| 8,398,538 B2 | 3/2013 | Dothie | |
| 8,403,865 B2 | 3/2013 | Halperin et al. | |
| 8,413,274 B2 | 4/2013 | Weismiller et al. | |
| 8,421,606 B2 | 4/2013 | Collins, Jr. et al. | |
| 8,428,696 B2 | 4/2013 | Foo | |
| 8,444,558 B2 | 5/2013 | Young et al. | |
| 8,469,884 B2 * | 6/2013 | David | A61B 5/0205 128/897 |
| 8,491,492 B2 | 7/2013 | Shinar et al. | |
| 8,517,953 B2 | 8/2013 | Lange et al. | |
| 8,620,615 B2 | 12/2013 | Oexman | |
| 8,672,853 B2 | 3/2014 | Young | |
| 8,679,034 B2 | 3/2014 | Halperin et al. | |
| 8,682,457 B2 | 3/2014 | Rawls-Meehan | |
| 8,725,311 B1 * | 5/2014 | Breed | G08B 21/06 600/300 |
| 8,769,747 B2 | 7/2014 | Mahoney et al. | |
| 8,840,564 B2 | 9/2014 | Pinhas et al. | |
| 8,872,640 B2 * | 10/2014 | Horseman | B60W 40/08 340/425.5 |
| 8,931,329 B2 | 1/2015 | Mahoney et al. | |
| 8,966,689 B2 | 3/2015 | McGuire et al. | |
| 8,973,183 B1 | 3/2015 | Palashewski et al. | |
| 8,984,687 B2 | 3/2015 | Stusynski et al. | |
| 2002/0124311 A1 | 9/2002 | Peftoulidis | |
| 2003/0045806 A1 | 3/2003 | Brydon | |
| 2003/0128125 A1 | 7/2003 | Burbank et al. | |
| 2003/0166995 A1 | 9/2003 | Jansen | |
| 2003/0182728 A1 | 10/2003 | Chapman et al. | |
| 2003/0221261 A1 | 12/2003 | Torbet et al. | |
| 2004/0049132 A1 | 3/2004 | Barron et al. | |
| 2005/0022606 A1 | 2/2005 | Partin et al. | |
| 2005/0038326 A1 | 2/2005 | Mathur | |
| 2005/0115561 A1 | 6/2005 | Stahmann et al. | |
| 2005/0190068 A1 | 9/2005 | Gentry et al. | |
| 2005/0283039 A1 | 12/2005 | Cornel | |
| 2006/0020178 A1 | 1/2006 | Sotos et al. | |
| 2006/0031996 A1 | 2/2006 | Rawls-Meehan | |
| 2006/0047217 A1 | 3/2006 | Mirtalebi | |
| 2006/0152378 A1 | 7/2006 | Lokhorst | |
| 2006/0162074 A1 | 7/2006 | Bader | |
| 2007/0118054 A1 | 5/2007 | Pinhas et al. | |
| 2007/0149883 A1 | 6/2007 | Yesha | |
| 2007/0179334 A1 | 8/2007 | Groves et al. | |
| 2007/0180047 A1 | 8/2007 | Dong et al. | |
| 2007/0180618 A1 | 8/2007 | Weismiller et al. | |
| 2007/0276202 A1 | 11/2007 | Raisanen et al. | |
| 2007/0290535 A1 * | 12/2007 | Meredith | B60N 2/42736 297/217.1 |
| 2008/0036252 A1 * | 2/2008 | Breed | B60J 10/00 297/217.2 |
| 2008/0052837 A1 | 3/2008 | Blumberg | |
| 2008/0071200 A1 | 3/2008 | Rawls-Meehan | |
| 2008/0077020 A1 | 3/2008 | Young et al. | |
| 2008/0092291 A1 | 4/2008 | Rawls-Meehan | |
| 2008/0092292 A1 | 4/2008 | Rawls-Meehan | |
| 2008/0092293 A1 | 4/2008 | Rawls-Meehan | |
| 2008/0092294 A1 | 4/2008 | Rawls-Meehan | |
| 2008/0093784 A1 | 4/2008 | Rawls-Meehan | |
| 2008/0097774 A1 | 4/2008 | Rawls-Meehan | |
| 2008/0097778 A1 | 4/2008 | Rawls-Meehan | |
| 2008/0097779 A1 | 4/2008 | Rawls-Meehan | |
| 2008/0104750 A1 | 5/2008 | Rawls-Meehan | |
| 2008/0104754 A1 | 5/2008 | Rawls-Meehan | |
| 2008/0104755 A1 | 5/2008 | Rawls-Meehan | |
| 2008/0104756 A1 | 5/2008 | Rawls-Meehan | |
| 2008/0104757 A1 | 5/2008 | Rawls-Meehan | |
| 2008/0104758 A1 | 5/2008 | Rawls-Meehan | |
| 2008/0104759 A1 | 5/2008 | Rawls-Meehan | |
| 2008/0104760 A1 | 5/2008 | Rawls-Meehan | |
| 2008/0104761 A1 | 5/2008 | Rawls-Meehan | |
| 2008/0109959 A1 | 5/2008 | Rawls-Meehan | |
| 2008/0109964 A1 | 5/2008 | Flocard et al. | |
| 2008/0109965 A1 | 5/2008 | Mossbeck | |
| 2008/0115272 A1 | 5/2008 | Rawls-Meehan | |
| 2008/0115273 A1 | 5/2008 | Rawls-Meehan | |
| 2008/0115274 A1 | 5/2008 | Rawls-Meehan | |
| 2008/0115275 A1 | 5/2008 | Rawls-Meehan | |
| 2008/0115276 A1 | 5/2008 | Rawls-Meehan | |
| 2008/0115277 A1 | 5/2008 | Rawls-Meehan | |
| 2008/0115278 A1 | 5/2008 | Rawls-Meehan | |
| 2008/0115279 A1 | 5/2008 | Rawls-Meehan | |
| 2008/0115280 A1 | 5/2008 | Rawls-Meehan | |
| 2008/0115281 A1 | 5/2008 | Rawls-Meehan | |
| 2008/0115282 A1 | 5/2008 | Rawls-Meehan | |
| 2008/0120775 A1 | 5/2008 | Rawls-Meehan | |
| 2008/0120776 A1 | 5/2008 | Rawls-Meehan | |
| 2008/0120777 A1 | 5/2008 | Rawls-Meehan | |
| 2008/0120778 A1 | 5/2008 | Rawls-Meehan | |
| 2008/0120779 A1 | 5/2008 | Rawls-Meehan | |
| 2008/0120784 A1 | 5/2008 | Warner et al. | |
| 2008/0122616 A1 | 5/2008 | Warner | |
| 2008/0126122 A1 | 5/2008 | Warner et al. | |
| 2008/0126132 A1 | 5/2008 | Warner | |
| 2008/0127418 A1 | 6/2008 | Rawls-Meehan | |
| 2008/0127424 A1 | 6/2008 | Rawls-Meehan | |
| 2008/0147442 A1 | 6/2008 | Warner | |
| 2008/0162171 A1 | 7/2008 | Rawls-Meehan | |
| 2008/0189865 A1 | 8/2008 | Bhai | |
| 2008/0275314 A1 | 11/2008 | Mack et al. | |
| 2008/0281611 A1 | 11/2008 | Rawls-Meehan | |
| 2008/0281612 A1 | 11/2008 | Rawls-Meehan | |
| 2008/0281613 A1 | 11/2008 | Rawls-Meehan | |
| 2008/0288272 A1 | 11/2008 | Rawls-Meehan | |
| 2008/0288273 A1 | 11/2008 | Rawls-Meehan | |
| 2008/0306351 A1 | 12/2008 | Izumi | |
| 2008/0307582 A1 | 12/2008 | Flocard et al. | |
| 2009/0018853 A1 | 1/2009 | Rawls-Meehan | |
| 2009/0018854 A1 | 1/2009 | Rawls-Meehan | |
| 2009/0018855 A1 | 1/2009 | Rawls-Meehan | |
| 2009/0018856 A1 | 1/2009 | Rawls-Meehan | |
| 2009/0018857 A1 | 1/2009 | Rawls-Meehan | |
| 2009/0018858 A1 | 1/2009 | Rawls-Meehan | |
| 2009/0037205 A1 | 2/2009 | Rawls-Meehan | |
| 2009/0043595 A1 | 2/2009 | Rawls-Meehan | |
| 2009/0058661 A1 * | 3/2009 | Gleckler | A61B 5/103 340/573.7 |
| 2009/0064420 A1 | 3/2009 | Rawls-Meehan | |
| 2009/0100599 A1 | 4/2009 | Rawls-Meehan | |
| 2009/0121660 A1 | 5/2009 | Rawls-Meehan | |
| 2009/0139029 A1 | 6/2009 | Rawls-Meehan | |
| 2009/0203972 A1 | 8/2009 | Heneghan et al. | |
| 2009/0275808 A1 | 11/2009 | DiMaio et al. | |
| 2009/0312998 A1 * | 12/2009 | Berckmans | G06F 19/3437 703/11 |
| 2009/0314354 A1 | 12/2009 | Chaffee | |
| 2010/0014711 A1 * | 1/2010 | Camhi | B60K 28/06 382/104 |
| 2010/0025900 A1 | 2/2010 | Rawls-Meehan | |
| 2010/0090383 A1 | 4/2010 | Rawls-Meehan | |
| 2010/0094139 A1 | 4/2010 | Brauers et al. | |
| 2010/0099954 A1 | 4/2010 | Dickinson et al. | |
| 2010/0152546 A1 | 6/2010 | Behan et al. | |
| 2010/0170043 A1 | 7/2010 | Young et al. | |
| 2010/0174198 A1 | 7/2010 | Young et al. | |
| 2010/0174199 A1 | 7/2010 | Young et al. | |
| 2010/0191136 A1 | 7/2010 | Wolford | |
| 2010/0199432 A1 | 8/2010 | Rawls-Meehan | |
| 2010/0231421 A1 | 9/2010 | Rawls-Meehan | |

(56) References Cited

U.S. PATENT DOCUMENTS

| | | |
|---|---|---|
| 2010/0302044 A1 | 12/2010 | Chacon et al. |
| 2010/0317930 A1 | 12/2010 | Oexman et al. |
| 2011/0001622 A1 | 1/2011 | Gentry |
| 2011/0010014 A1 | 1/2011 | Oexman et al. |
| 2011/0015495 A1 | 1/2011 | Dothie et al. |
| 2011/0041592 A1 | 2/2011 | Schmoeller et al. |
| 2011/0068935 A1 | 3/2011 | Riley et al. |
| 2011/0087113 A1 | 4/2011 | Mack et al. |
| 2011/0094041 A1 | 4/2011 | Rawls-Meehan |
| 2011/0115635 A1 | 5/2011 | Petrovski et al. |
| 2011/0144455 A1 | 6/2011 | Young et al. |
| 2011/0156915 A1 | 6/2011 | Brauers et al. |
| 2011/0224510 A1 | 9/2011 | Oakhill |
| 2011/0239374 A1 | 10/2011 | Rawls-Meehan |
| 2011/0252569 A1 | 10/2011 | Rawls-Meehan |
| 2011/0258784 A1 | 10/2011 | Rawls-Meehan |
| 2011/0282216 A1 | 11/2011 | Shinar et al. |
| 2011/0283462 A1 | 11/2011 | Rawls-Meehan |
| 2011/0291795 A1 | 12/2011 | Rawls-Meehan |
| 2011/0291842 A1 | 12/2011 | Oexman |
| 2011/0295083 A1 | 12/2011 | Doelling et al. |
| 2011/0302720 A1 | 12/2011 | Yakam et al. |
| 2011/0306844 A1 | 12/2011 | Young |
| 2012/0025992 A1 | 2/2012 | Tallent et al. |
| 2012/0053423 A1 | 3/2012 | Kenalty et al. |
| 2012/0053424 A1 | 3/2012 | Kenalty et al. |
| 2012/0056729 A1 | 3/2012 | Rawls-Meehan |
| 2012/0057685 A1 | 3/2012 | Rawls-Meehan |
| 2012/0086249 A1* | 4/2012 | Hotary ................ B60N 2/0228 297/284.3 |
| 2012/0090698 A1 | 4/2012 | Giori et al. |
| 2012/0101395 A1* | 4/2012 | Fujita ..................... A61B 5/024 600/508 |
| 2012/0110738 A1 | 5/2012 | Rawls-Meehan |
| 2012/0110739 A1 | 5/2012 | Rawls-Meehan |
| 2012/0110740 A1 | 5/2012 | Rawls-Meehan |
| 2012/0112890 A1 | 5/2012 | Rawls-Meehan |
| 2012/0112891 A1 | 5/2012 | Rawls-Meehan |
| 2012/0112892 A1 | 5/2012 | Rawls-Meehan |
| 2012/0116591 A1 | 5/2012 | Rawls-Meehan |
| 2012/0119886 A1 | 5/2012 | Rawls-Meehan |
| 2012/0119887 A1 | 5/2012 | Rawls-Meehan |
| 2012/0138067 A1 | 6/2012 | Rawls-Meehan |
| 2012/0154155 A1 | 6/2012 | Brasch |
| 2012/0186019 A1 | 7/2012 | Rawls-Meehan |
| 2012/0198632 A1 | 8/2012 | Rawls-Meehan |
| 2012/0311790 A1 | 12/2012 | Nomura et al. |
| 2013/0009761 A1* | 1/2013 | Horseman ............. B60W 40/08 340/425.5 |
| 2013/0013331 A1* | 1/2013 | Horseman ........... G06F 19/3418 705/2 |
| 2013/0160212 A1 | 6/2013 | Oexman et al. |
| 2013/0174347 A1 | 7/2013 | Oexman et al. |
| 2013/0227787 A1 | 9/2013 | Herbst et al. |
| 2013/0342366 A1* | 12/2013 | Kiefer ..................... G08B 6/00 340/901 |
| 2014/0001799 A1* | 1/2014 | Kalisz .................. B60R 21/207 297/216.1 |
| 2014/0007656 A1 | 1/2014 | Mahoney |
| 2014/0097651 A1* | 4/2014 | Fortune ................ B60N 2/5685 297/180.12 |
| 2014/0137332 A1 | 5/2014 | McGuire et al. |
| 2014/0182061 A1 | 7/2014 | Zaiss |
| 2014/0250597 A1 | 9/2014 | Chen et al. |
| 2014/0257571 A1 | 9/2014 | Chen et al. |
| 2014/0259417 A1 | 9/2014 | Nunn et al. |
| 2014/0259418 A1 | 9/2014 | Nunn et al. |
| 2014/0259419 A1 | 9/2014 | Stusynski |
| 2014/0259431 A1 | 9/2014 | Fleury |
| 2014/0259433 A1 | 9/2014 | Nunn et al. |
| 2014/0259434 A1 | 9/2014 | Nunn et al. |
| 2014/0265492 A1* | 9/2014 | Larsen ................ F16K 99/0028 297/284.1 |
| 2014/0277611 A1 | 9/2014 | Nunn et al. |
| 2014/0277778 A1 | 9/2014 | Nunn et al. |
| 2014/0277822 A1 | 9/2014 | Nunn et al. |
| 2014/0313700 A1 | 10/2014 | Connell et al. |
| 2015/0007393 A1 | 1/2015 | Palashewski et al. |
| 2015/0025327 A1 | 1/2015 | Young et al. |
| 2015/0026896 A1 | 1/2015 | Fleury et al. |
| 2015/0136146 A1 | 5/2015 | Hood et al. |
| 2015/0157137 A1 | 6/2015 | Nunn et al. |
| 2015/0157519 A1 | 6/2015 | Stusynski et al. |
| 2015/0182033 A1 | 7/2015 | Brosnan et al. |
| 2015/0182397 A1 | 7/2015 | Palashewski et al. |
| 2015/0182399 A1 | 7/2015 | Palashewski et al. |
| 2015/0182418 A1 | 7/2015 | Zaiss |
| 2015/0210192 A1* | 7/2015 | Benson .................. B60N 2/505 297/217.2 |

OTHER PUBLICATIONS

U.S. Appl. No. 14/146,327, filed Jan. 2, 2014, Palashewski et al.
U.S. Appl. No. 14/283,675, filed May 21, 2014, Mahoney et al.
U.S. Appl. No. 14/675,355, filed Mar. 31, 2015, Palashewski et al.
U.S. Appl. No. 14/687,633, filed Apr. 15, 2015, Brosnan et al.

* cited by examiner

SMART SEAT MONITORING SYSTEM

FIELD OF THE INVENTION

The present disclosure pertains to a seat monitoring system for monitoring vital signs and position of the subject present in a seat, such as a smart seat.

BACKGROUND

Monitoring a condition of a subject, such as vital signs including heart rate and respiration rate, can require expensive equipment, such as an electrocardiogram (EKG), a ballistocardiograph (BCG), a piezoelectric film, or an array of sensors. In addition to being prohibitively expensive for many situations, both EKGs and BCGs can be too cumbersome for use outside of medical facilities. EKGs, for example, typically necessitate attaching electrodes to the bodies of subjects, while BCGs rely on large, heavy, and unaesthetic force-measuring platforms. Some systems can also monitor the condition of presence or absence of a subject, but cannot monitor changes in position of the subject or accurately predict when a subject's position should change to benefit the subject.

SUMMARY

An array of sensors used to communicate with a pump capable of regulating the fluid pressure within one or more layers of fluid bladders can additionally be leveraged to detect conditions including position, heart rate, and respiratory rate of a subject in pressure contact with the one or more layers. An example use of this system is embodied in a smart seat that can monitor various conditions of a subject, the smart seat including at least one layer of fluid bladders. A pump is in fluid communication with at least one layer of fluid bladders, the pump operable to increase or decrease a fluid pressure within each fluid bladder in the layer. The array of sensors is also in fluid communication with each fluid bladder in at least one layer of fluid bladders, the array of sensors operative to determine a pressure within each fluid bladder in the layer. A controller is configured to determine one or more conditions of the subject based on the pressure within at least one layer of fluid bladders. The fluid bladder and sensor system can be less cumbersome to use compared to many monitoring devices, and can be used outside of a medical center environment, for example, in a smart seat.

Another example of a seat monitoring system comprises a first layer of one or more fluid bladders packaged within a seat, a pump in fluid communication with the first layer, the pump operable to increase fluid pressure of each bladder within the first layer, an array of one or more sensors in fluid communication with the first layer and operative to sense pressure and pressure changes within each bladder within the first layer and a controller configured to: collect pressure data; determine from the pressure data a monitored parameter relevant to a subject in the seat; and change an aspect of the seat based on the monitored parameter.

Methods of using the smart seat system are also disclosed. One method of monitoring a subject in a seat comprises collecting with a computer data from a smart seat system when a subject is seated in the smart seat system. The smart seat system comprises a first layer of one or more fluid bladders packaged within a seat cushion, a pump in fluid communication with the first layer, the pump operable to increase fluid pressure of each bladder within the first layer and an array of one or more sensors in fluid communication with the first layer and operative to sense pressure and pressure changes within each bladder within the first layer. The data comprises one or more of: absolute pressure of the one or more fluid bladders over time; at least one of a heart rate and a respiration rate of the subject over time based on a first range of pressure changes in at least one of the one or more bladders; length of sitting episodes of the subject in the seat over time; and shifting of the subject in the seat during the sitting episodes based on a second range of pressure changes in the one or more bladders. A monitored parameter relevant to the subject is determined from the data and the fluid pressure in one of the one or more fluid bladders is changed in response to the monitored parameter.

BRIEF DESCRIPTION OF THE DRAWINGS

The description herein makes reference to the accompanying drawings, wherein like reference numerals refer to like parts throughout the several views, and wherein.

DETAILED DESCRIPTION

Figure 1:
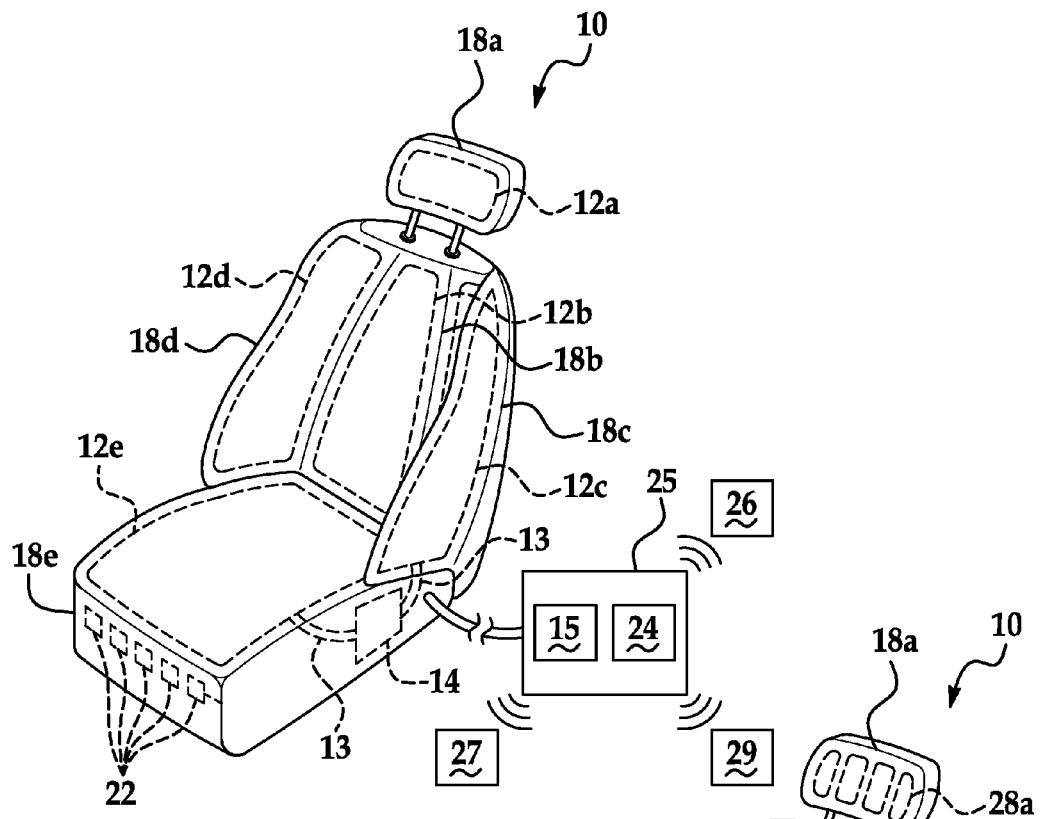
FIG. 1 is perspective view of a smart seat including a layer of fluid bladders, at least one fluid bladder in the layer configured to measure at least one vital sign of a subject in the smart seat.

FIG. 1 is perspective view of a smart seat 10. The smart seat can be any type of seat in which a subject sits for an extended period of time. Examples include a driver's seat in an automobile, including semi tractor-trailers, bus, train, airplane and the like. Examples also include an office desk chair or any other chair in which the occupant desires to stay alert. Examples also include a home chair or similar in which the subject sits for extended periods of time and desires to have some aspect of his or her biology monitored.

The smart seat in FIG. 1 includes a layer of fluid bladders 12a-e, at least one fluid bladder in the layer, e.g. fluid bladder 12b, configured to measure at least one vital sign of a subject in the smart seat 10. The seat 10 can also include a plurality of cushions 18*a-e*. For example, the seat 10 can include a headrest cushion 18*a*, a back cushion 18*b*, side cushions 18*c*, 18*d*, and a lower cushion 18*e*. Each of the cushions 18*a-e* can contain one of the fluid bladders 12*a-e*. For example, the lower cushion 18*e* includes the fluid bladder 12*e* as shown in FIG. 1. In addition to the fluid bladders 12*a-e*, the cushions 18*a-e* can include filling such as foam padding, springs, additional fluid bladders (described below), spring-based padding, and/or another type of foam or padding that offers flexibility and/or softness.

Each of the bladders 12*a-e* can hold air or another fluid. In addition to holding air or another fluid, the bladders 12*a-e* can enclose foam or another material through which fluid waves of an expected magnitude can propagate a sufficient distance without becoming too dampened. The fluid bladders 12*a-e* can be sized to have a surface area nearly as large as the surface area of the respective cushions 18*a-e* in which they are encased. Alternatively, one or more of the bladders 12*a-e* can have a smaller size. For example, the fluid bladder 12*b* can cover an area of the back cushion 18*b* in front of which the subject's heart and/or lungs are expected to be positioned (e.g., a one foot by one foot square for an adult). Even if the subject is positioned on the seat 10 such that the subject's heart and/or lungs are not directly above the fluid bladder 12*b*, pressure fluctuations caused by the subject may still be received by the fluid bladder 12*b*.

The pressure in the bladders 12*a-e* can vary depending on the amount of fluid in the bladders 12*a-e*, whether a subject is compressing the bladders 12*a-e* by sitting in the seat 10, the heart rate of the subject compressing the bladders 12*a-e*, the respiration rate of the subject compressing the bladders 12*a-e*, other movements of the subject sitting in the seat 10 (e.g., rolling of the trunk or movement of the limbs), the temperature of the fluid in the bladders 12*a-e*, and other considerations.

The seat 10 can include, or be coupled to, a pump 14 and a control unit 15 as shown. The pump 14 can be a separate unit from the bladders 12*a-e* and can be fluidly coupled to inlets of the bladders 12*a-e* via a hose or network of hoses (for example, such as hoses 13). Alternatively, multiple pumps can be present, with one or more pumps integral with each bladder 12*a-e* such that the pumps can output high pressure fluid directly into the bladders 12*a-e* instead of through the hoses. The pump 14 can be a rotary type pump or any other type of pump. The pump 14 can include an electric line for connection to an outlet or another power source or be wired into the vehicle system, and the pump can also include a data line for communication with the control unit 15. Alternatively, the pump 14 can include a self-contained power source, such as one or more batteries.

Figure 2:
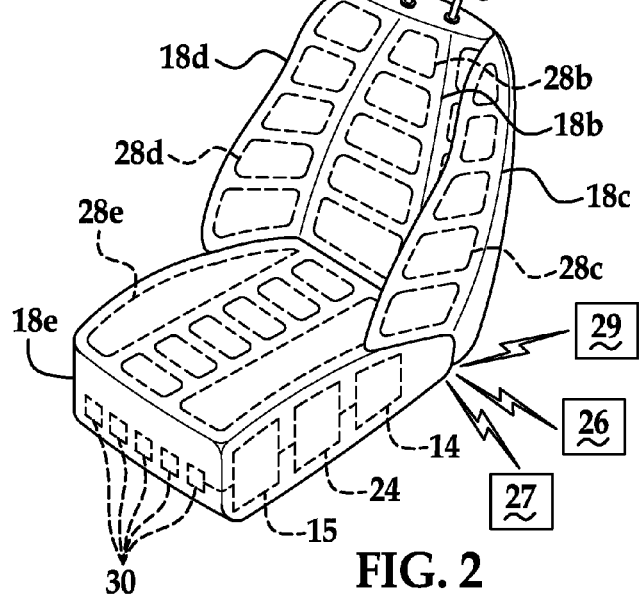
FIG. 2 is a perspective view of a smart seat including a layer of fluid bladder grids for adjusting the position of the subject in the smart seat.

The pump 14 can be disposed within the smart seat 10, such as the seat cushion as a non-limiting example and shown in FIG. 2, and in communication with one or more sensors 22, each sensor of sensors 22 in communication with one of the bladders 12*a-e*. The pump can also communicate with a controller 24 in communication with both the array of sensors 22 and the control unit 15. Also, the pump 14 can include a fluid inlet and a pressurized fluid outlet. Fluid at an ambient pressure can be received by the pump 14 through the inlet, and the pump can increase the pressure of the fluid before outputting the fluid through the outlet (not shown). The pump 14 can also be disposed external to the smart seat 10.

The array of sensors 22 can include semiconductor sensors or another type of sensors. The array of sensors 22 can be configured such that each sensor in the array can detect an amount of air pressure in one of the bladders 12*a-e* of the smart seat 10. That is, the air pressure detected by each sensor can indicate the air pressure in one of the bladders 12*a-e*. While operation of the pump 14 may affect the pressure detected by the array of sensors 22, the pump 14 can operate only as required to maintain a predetermined pressure within the bladders 12*a-e* (e.g., to replace any fluid that seeps out of the bladders 12*a-e*). Additionally, the array of sensors 22 can draw power from a power source that also powers the pump 14.

The array of sensors 22 can output pressure signals to the controller 24. The array of sensors 22 can be hard-wired to the controller 24 (through the control unit 15 as shown), the array of sensors 22 can wirelessly communicate with the controller 24 by way of a transmitter using, for example, a standard wireless protocol (e.g., IEEE 802.11, RF, Bluetooth, or 3G), or the array of sensors 22 can otherwise be coupled to the controller 24 for communication therewith.

The controller 24, which can be a processor, microprocessor, multiple processors, or any other device including one or more memories and a CPU for executing a program stored in the memory, can control a motor in the pump 14 to produce pressurized air in the outlet portion of the pump 14. The controller 24 can be hard-wired to the motor or be in wireless communication with the motor using, for example, a standard wireless protocol. As a result, the controller 24 can control the operation of the pump 14. For example, the controller 24 can control the pump 14 in response to any one of the pressure signals by instructing the pump 14 to inflate one or more of the bladders 12*a-e* when the controller 24 determines the air pressure in a given bladder 12*a-e* is below a set amount.

Thus, when the controller 24 actuates the motor, the motor can produce pressurized air in the outlet that passes from the pump 14 through one of the hoses into one of the bladders 12*a-e* to increase the fluid pressure inside one of the bladders 12*a-e*. The controller 24 can also be in communication with an air release valve or other structure for releasing air from the bladders 12*a-e* such that the controller 24 can provide an instruction to decrease the fluid pressure in the bladders 12*a-e*.

Additionally, the controller 24 can analyze the pressure signals to determine a heart rate, respiration rate, and/or other vital signs of a subject compressing one or more of the cushions 18*a-e* of the smart seat 10. More specifically, when a subject sits on the seat 10, each of the subject's heart beats, breaths, and other movements can create a force on one or more of the cushions 18*a-e* that is transmitted to one or more of the bladders 12*a-e*. As a result of the force input to the bladders 12*a-e* from the subject's movement, a wave can propagate through the bladders 12*a-e*, into one or more of the hoses, and arrive at the pump 14. The array of sensors 22 can detect these waves, and thus the pressure signals output by the array of sensors 22 can indicate a heart rate, respiratory rate, or other information regarding the subject.

To overcome a DC offset in the pressure signals, the pressure signals can pass through a circuit splitting the pressure signals into a DC coupled path and an AC coupled path, and the AC coupled path can be amplified and filtered. The controller 24 can perform a pattern recognition algorithm or other calculation based on the amplified and filtered pressure signals to determine the user's heart rate and respiratory rate. For example, the algorithm or calculation can be based on assumptions that a heart rate portion of a pressure signal has a frequency in the range of 0.5-4.0 Hz and that a respiration rate portion of a pressure signal has a frequency in the range of less than 1 Hz. The controller 24 can also be configured to determine other characteristics of a subject based on the pressure signals, such as blood pressure, tossing and turning movements, rolling movements, limb movements, weight, the presence or lack or presence of a subject, and/or the identity of the subject. The controller 24 can also output a data indicating the characteristics of the subject (e.g., heart rate and respiratory rate) to the control unit 15.

As illustrated in FIG. 1, the control unit 15 and controller 24 can be externally connected to the smart seat 10 via a wire or wirelessly. A control box 25 may include the control unit 15 and controller 24, as well as one or more of a power supply, processor, memory, switches, and analog to digital (A/D) converter. Switches may be, for example, a relay or a solid state switch. Switches may be located in the pump 14 rather than the control box 25. As illustrated in FIG. 2, the control unit 15 and controller 24 can be internal to the smart seat 10. The control unit 15 and controller 24 are illustrated as separate devices but can be combined into one unit.

The control unit 15 or control box 25 can include a transmitter that can relay the data to an external database or other external device 26. The transmitter can be a wireless transmitter operating using a standard wireless protocol for communication with the database or other external device 26, though the transmitter can alternatively be hardwired to the database or other external device using a phone line, Ethernet line, or other physical connection. For example, the network interface may be configured to use the 802.11 standards (e.g., 802.11a/b/c/g/n/ac), PAN network standards such as 802.15.4 or Bluetooth, infrared, cellular standards (e.g., 3G/4G etc.), Ethernet, and USB for receiving and transmitting data. The previous list is not intended to exhaustive and other protocols may be used. Not all components need to be configured to use the same protocols.

As a result, the database or other external device 26 can store information produced as a result of the data, and the subject can be alerted to issues based on either short-term or long-term trends related to their vital signs or provided with other communications regarding their sedentary state, fitness level, cardiovascular condition, or other health information. The external device 26 can include or be in communication with a display device 27 in the vehicle, such as a screen that can display information relayed in the status signals, such as the subject's heart rate, respiratory rate, amount of time spent in the smart seat 10, and other considerations. An alerting system 29 can alert a driver or other subject of a threshold, potential problem, need for change, etc. The alerting system can also be incorporated into the display 27.

In one example, the database or other external device 26 can store a log of status signals, and the controller 24 or another computing device with processing capability can create a sleepiness threshold based on one or more vital signs. The alerting system 29 can alert the driver when the sleepiness threshold indicates the driver is drowsy.

The control unit 15 can also be hard-wired or in wireless communication with the controller 24 for controlling operation of the pump 14. The control unit 15 can be used to send signals to the controller 24 to increase the air pressure in one or more of the bladders 12*a-e*. As another example, the control unit 15 can be used to instruct the array of sensors 22 and/or the controller 24 to operate in a privacy mode in which data is not detected, retained, displayed, transmitted, and/or analyzed, or to communicate with the database or other external device 26 to obtain stored information regarding a subject's vital signs. The database or external device 26 can be accessed via the control unit 15 or a separate computing device (e.g., via the internet.) Components such as a temperature controller, vibration controller, etc. can also be incorporated into the system, for example, into the control box 25.

The smart seat 10 monitoring system can have a different structure from illustrated. For example, the pump 14 can include the transmitter instead of the control unit 15. In another example, the control unit 15 can be configured to activate the alerting system 29 if the subject's heat rate or respiration rate slows to a point indicating a certain level of sleepiness or lack of attention. The alarm can be audible in that one or more vehicle systems in communication with the control unit can be instructed to alert the subject in the smart seat 10. The alarm can also be haptic, for example, the cushions 18*a-e* of the smart seat 10 can be manipulated using fluctuations in pressure of the bladders 12*a-e* until measures of the subject's vital signs indicate that the subject has regained a level of attention necessary to operate the vehicle.

FIG. 2 is a perspective view of a smart seat 10 including a layer of fluid bladder grids 28*a-e* for adjusting the position of the subject in the smart seat 10. As shown, each of the cushions 18*a-e* includes its own grid of fluid bladders 28*a-e*, allowing for inflation and deflation in targeted areas of the cushions 18*a-e*. The pump 14 described in FIG. 1 can be in communication with each of the grids of fluid bladders 28*a-e* through one or more hoses (not shown). The pump 14 is also in communication with the controller 24 and control unit 15 as described in FIG. 1. Finally, the pump 14 in communication with an array of seat actuators 30, each actuator in the array of seat actuators 30 in communication with one of the grids of fluid bladders 28*a-e* and configured to inflate and deflate specific regions of the grids of fluid bladders 28*a-e* based on the commands received from the control unit 15.

For example, the grids of fluid bladders 28*a-e* can be packaged in the smart seat 10 either above or below the layer of fluid bladders 12*a-e* for monitoring vital signs described above in relation to FIG. 1. The grids of fluid bladders 28*a-e* can also be used to provide haptic feedback through the cushions 18*a-e* of the smart seat 10 if the layer of fluid bladders 12*a-e* measures vital signs of the subject in the smart seat 10 that indicate inattentiveness or sleepiness. In addition to pulsing, oscillating, or vibration based haptic feedback, the grids of fluid bladders 28*a-e* can be configured to iteratively inflate and deflate in a manner that could massage or stretch specific regions of the subject's body to negate the effects of inattentiveness or sleepiness.

As another example, the grids of fluid bladders 28*a-e* can be used to move or manipulate the position of specific areas on a subject's torso or limbs that have remained motionless for a threshold period of time, inflating or deflating the relevant portion of the grid of fluid bladders 28*a-e* such that the specific area is moved, nudged, or manipulated. Occasional movement of torso or limbs can encourage blood flow in the region and help keep the torso or limb from "falling asleep" due to lack of movement or pressure on the nervous system from the smart seat 10 or other parts of the subject's body. The signal received by the array of seat actuators 30 to target specific areas of the subject's body for movement is based on a determination of the position of the subject. Positional determination of the subject in the smart seat 10 is described in respect to FIGS. 3 and 4.

Figure 3:
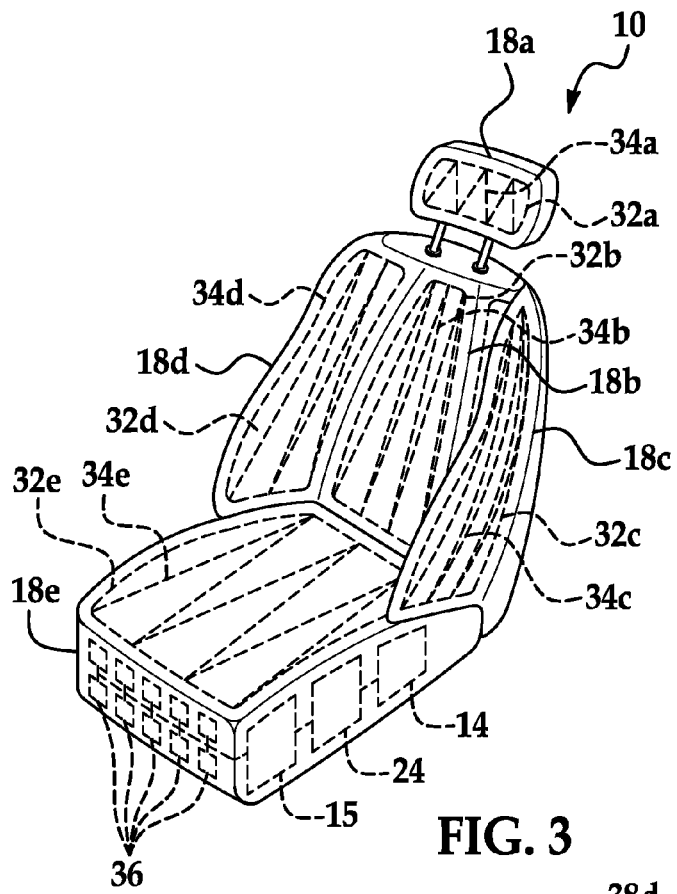
FIG. 3 is a perspective view of a smart seat including a layer of fluid bladders each including a vertical seam for determining the vertical position of the subject in the smart seat.

FIG. 3 is a perspective view of a smart seat 10 including a layer of fluid bladders 32*a-e* each including a vertical seam 34*a-e* for determining the vertical position of the subject in the smart seat 10. "Vertical" refers to a for-aft direction of the seat, as opposed to "horizontal", which refers to side to side along the seat. The layer of fluid bladders 32a-e can be positioned above or below the layer of fluid bladder grids 28a-e shown in FIG. 2 for adjusting the position of the subject in the smart seat 10. The layer of fluid bladders 32a-e can also be positioned above or below the layer of fluid bladders 12a-e used to determine the condition of the subject or can be integral with the fluid bladders 12a-e, that is, fluid bladders 12a-e and fluid bladders 32a-e may be a single layer of fluid bladders used to determine various conditions of the subject including heart rate, respiration rate, and vertical position.

Each vertical seam 34a-e splits its respective fluid bladder 32a-e into two halves in a vertical zig-zag pattern. Each half of each fluid bladder 32a-e includes fingers, or teeth, that extend between the fingers, or teeth, of the other half. Though the fingers shown in FIG. 3 are triangular, they can also be in any other shape. The design is configured such that the halves are interleaved, allowing each half of each fluid bladder 32a-e to sense position in a linear manner. By separating the fluid bladders 32a-e into interleaved halves, the pressure can be measured independently in each half.

In one example, the fluid bladders 32a-e can include or be in communication with an array of sensors 36. The array of sensors 36 can be configured to measure the pressure independently in each half of the fluid bladders 32a-e. In the example shown in FIG. 3, ten sensors are shown in the array of sensors 36, with each sensor measuring pressure in one half of a fluid bladder, for example, fluid bladder 32a. The pressure in the top half of each fluid bladder 32a-e will increase linearly as a subject moves toward the top of the smart seat 10. In a similar manner, the pressure in the bottom half of each fluid bladder 32a-e will increase linearly as the subject moves toward the bottom (or front, for fluid bladder 32e) of the smart seat 10. The difference in pressure between the halves of the fluid bladders 32a-e can be used to represent the vertical and fore/aft position of the subject sitting in the smart seat 10.

The pressure differential between the top and bottom halves of the fluid bladders 32a-e is also useful for capturing positional data over time and feeding the results to the control unit 15 to send commands to the pump 14 to inflate or deflate the fluid bladders 28a-e to manipulate the position of the subject in the smart seat 10. By capturing a string, or stream, of pressure differentials while the subject moves along, is pressed into, or is motionless on the fluid bladders 32a-e, the forces experienced by the subject or the inertia of the subject in the smart seat 10 can be determined. If a pattern of pressure differentials is captured indicating inertia of the subject or forces acting on the subject in one direction for more than a threshold period of time, the control unit 15 can be configured to send a command to the pump 14 to inflate or deflate one or more of the fluid bladders 28a-e to reposition the subject in the smart seat 10.

Figure 4:
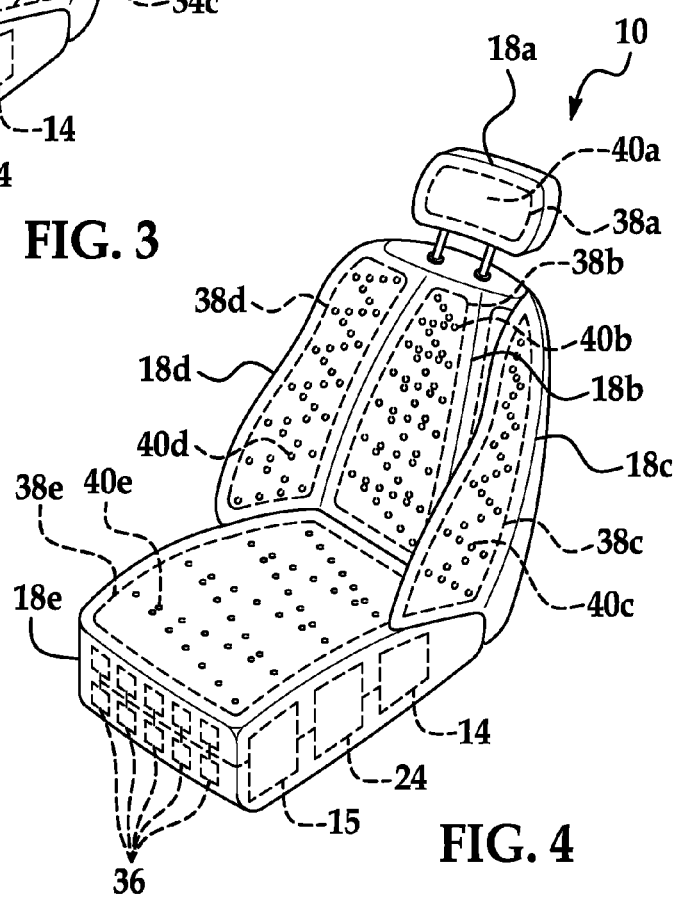
FIG. 4 is a perspective view of a smart seat including a layer of fluid bladders each including a horizontal seam for determining the horizontal position of the subject in the smart seat.

FIG. 4 is a perspective view of a smart seat 10 including a layer of fluid bladders 38a-e each including a horizontal seam 40a-e for determining the horizontal position of the subject in the smart seat 10. The layer of fluid bladders 38a-e can be positioned above or below the layer of fluid bladder grids 28a-e shown in FIG. 2 for adjusting the position of the subject in the smart seat 10 and above or below the layer of fluid bladders 32a-e for determining the vertical or fore/aft position of the subject. The layer of fluid bladders 38a-e can also be positioned above or below the layer of fluid bladders 12a-e used to determine the condition of the subject or can be integral with the fluid bladders 12a-e, that is, fluid bladders 12a-e and fluid bladders 38a-e may be one set of fluid bladders used to determine various conditions of the subject including heart rate, respiration rate, and position. In the case of integrated bladders to determine the various conditions of the subject, only one array of fluid bladders 32a-e or fluid bladders 38a-e can be integral with fluid bladders 12a-e, not both, as the horizontal and vertical position determinations are separate and based on the vertical seams 34a-e and horizontal seams 40a-e.

Each horizontal seam 40a-e splits its respective fluid bladder 38a-e into two halves in a horizontal zig-zag pattern. Each half of each fluid bladder 38a-e includes fingers, or teeth, that extend between the fingers, or teeth, of the other half. Though the fingers shown in FIG. 4 are triangular, they can also be in any other shape. The design is configured such that the halves are interleaved, allowing each half of each fluid bladder 38a-e to sense position in a linear manner. By separating the fluid bladders 38a-e into interleaved halves, the pressure can be measured independently in each half.

In one example, the fluid bladders 38a-e can include or be in communication with the array of sensors 36 as described in FIG. 3. The pressure in the left half of each fluid bladder 38a-e will increase linearly as a subject moves toward the left side of the smart seat 10. In a similar manner, the pressure in the right half of each fluid bladder 38a-e will increase linearly as the subject moves toward the right side of the smart seat 10. The difference in pressure between the halves of the fluid bladders 38a-e can be used to represent the horizontal position of the subject sitting on in the smart seat 10. As was described in reference to FIG. 3, the pressure differential between the left and right halves of the fluid bladders 38a-e is also useful for capturing positional data over time and feeding the results to the control unit 15 to send commands to the pump 14 to inflate or deflate the fluid bladders 28a-e to manipulate the position of the subject in the smart seat 10.

Figure 5:
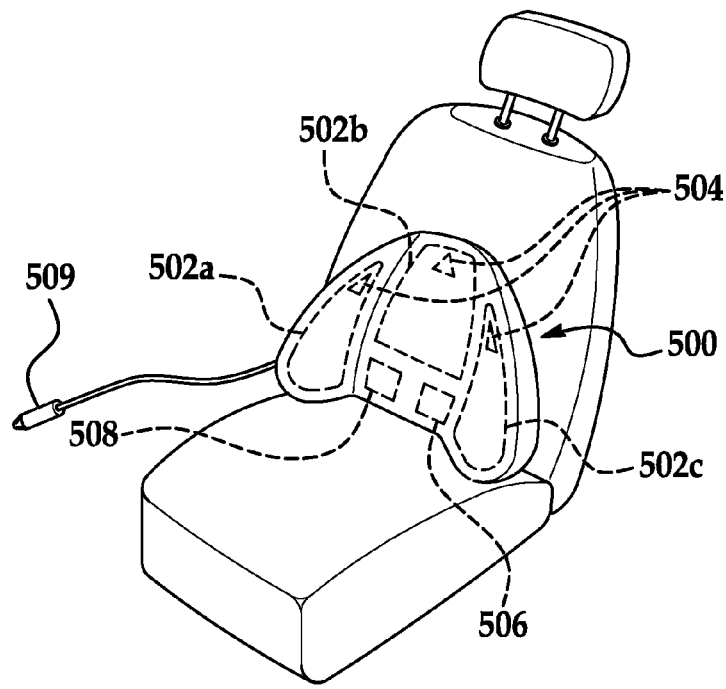
FIG. 5 is a perspective view of a seat back support including a layer of fluid bladders, at least one fluid bladder in the layer configured to measure velocity of a subject pressing against the back support.

FIG. 5 is a perspective view of a seat back support 500 including a layer of fluid bladders 502 a-c, at least one fluid bladder in the layer of fluid bladders 502a-c including one or more sensors 504 configured to measure velocity of a subject pressing against the back support 500. The velocity measurement can be an important measure in the context of automotive racing or in use of high speed sports cars, where repetitive or prolonged gravitational forces (g-forces) experienced by the driver can cause fatigue or injury depending on the duration of time and the direction in which the g-forces are experienced.

The one or more sensors 504 measuring velocity can be accelerometers or any other sensors capable of determining velocity experienced by the driver. The velocity can also be measured by the one or more sensors 504 in any or all sections of the layer of fluid bladders, e.g. in bladder 502a, bladder 502b, or bladder 502c to allow directional g-forces to be calculated, that is, whether the driver is being forced to the center, right side, or left side of the back support 500. The one or more sensors 504 can be in communication, either wired or wirelessly, with a control unit 506 included in the back support. The control unit 506 can include a processor, microprocessor, multiple processors, or any other device including one or more memories and a processor for executing a program stored in the memory. Velocity data and time duration can be stored the memory of the control unit 506 and used to determine pressure changes needed within the layer of fluid bladders 502a-c.

For example, the control unit 506 can be in communication with an integrated pump 508 that is in fluid communication with the layer of fluid bladders 502a-c and can send signals to increase or decrease pressure within one or more of the fluid bladders 502a-c based on velocity data captured and time duration of the given velocity. If the subject is pressed against the back of the support or one of the sides of the support, the relevant section can be inflated (or deflected) to provide additional (or lesser) support or rotate the subject back into a central position since a twisted position can cause strain. The back support 500 can be connected to a power source in a vehicle using adaptor 509, can be powered by a battery, or can be powered by any other means sufficient to provide power to the one or more sensors 504, the control unit 506, and the pump 508. The layer of fluid bladders 502a-c in the back support can also be actuated based on the measured position of the subject. Positional determination of the subject against the back support 500 is described in respect to FIGS. 6 and 7.

Figure 6:
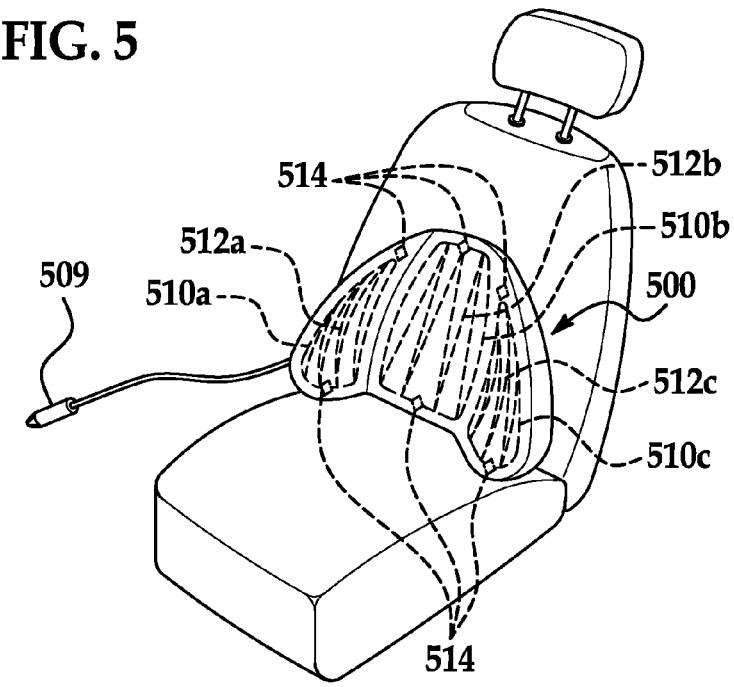
FIG. 6 is a perspective view of a seat back support including a layer of fluid bladders including a vertical seam for determining the vertical position of the subject pressing against the back support.

FIG. 6 is a perspective view of a seat back support 500 including a layer of fluid bladders 510a-c each including a vertical seam 512a-c for determining the vertical position of the subject pressing against the back support 500. The layer of fluid bladders 510a-c can be positioned above or below the layer of fluid bladders 502a-c shown in FIG. 5 for measuring the vital signs and velocity of the subject in the smart seat 10. Each vertical seam 512a-c splits its respective fluid bladder 510a-c into two halves in a vertical zig-zag pattern. Each half of each fluid bladder 510a-c includes fingers, or teeth, that extend between the fingers, or teeth, of the other half. Though the fingers shown in FIG. 6 are triangular, they can also be in any other shape. The design is configured such that the halves are interleaved, allowing each half of each fluid bladder 510a-c to sense position in a linear manner. By separating the fluid bladders 510a-c into interleaved halves, the pressure can be measured independently in each half.

In one example, the fluid bladders 510a-c can include or be in communication with an array of sensors 514. The array of sensors 514 can be configured to measure the pressure independently in each half of the fluid bladders 510a-c. In the example shown in FIG. 6, six sensors are shown in the array of sensors 36, with each sensor measuring pressure in one half of a fluid bladder, for example, fluid bladder 510a. The pressure in the top half of each fluid bladder 510a-c will increase linearly as a subject moves or pivots toward the top of the back support 500. In a similar manner, the pressure in the bottom half of each fluid bladder 510a-c will increase linearly as the subject moves toward the bottom of the back support 500. The difference in pressure between the halves of the fluid bladders 510a-c can be used to represent the vertical position of the subject sitting against the back support 500.

The pressure differential between the top and bottom halves of the fluid bladders 510a-c is also useful for capturing positional data over time and feeding the results to the control unit 506 to send commands to the pump 508 to inflate or deflate the fluid bladders 502a-c to manipulate the position of the subject against the back support 500. By capturing a string, or stream, of pressure differentials while the subject moves along, is pressed into, or is motionless on the fluid bladders 510a-c, the forces experienced by the subject or the inertia of the subject against the back support 500 can also be determined. If a pattern of pressure differentials is captured indicating inertia of the subject or forces acting on the subject in one direction for more than a threshold period of time, the control unit 506 can be configured to send a command to the pump 508 to inflate or deflate one or more of the fluid bladders 502a-c to reposition the subject against the back support 500.

Figure 7:
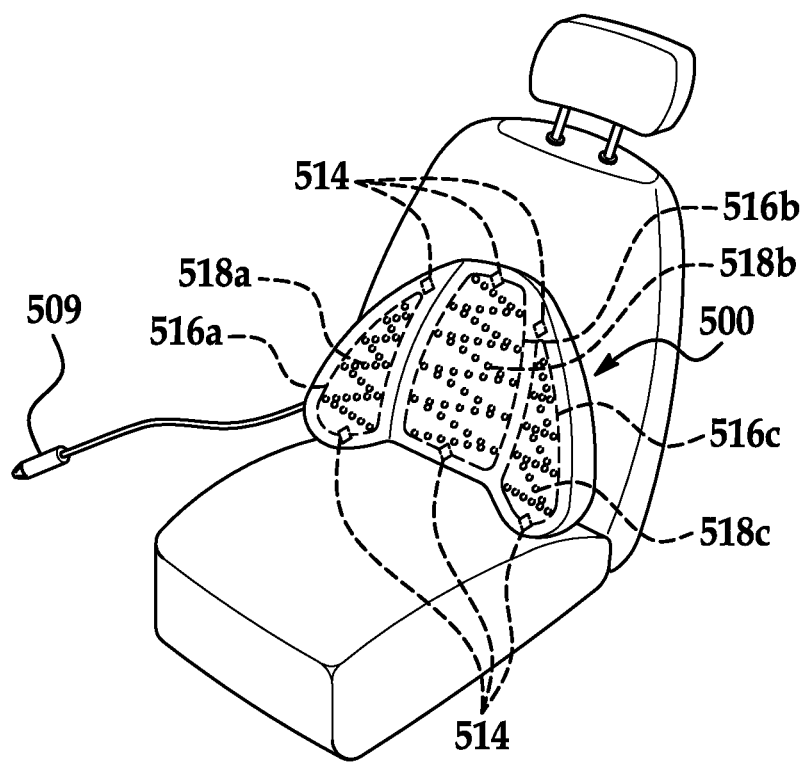
FIG. 7 is a perspective view of a seat back support including a layer of fluid bladders including a horizontal seam for determining the horizontal position of the subject pressing against the back support.

FIG. 7 is a perspective view of a seat back support 500 including a layer of fluid bladders 516a-c each including a horizontal seam 518a-c for determining the horizontal position of the subject pressing against the back support 500. The layer of fluid bladders 516a-c can be positioned above or below the layer of fluid bladders 510a-c for determining the vertical or position of the subject. The layer of fluid bladders 516a-c can also be positioned above or below the layer of fluid bladders 502a-c used to determine vital signs and velocity of the subject. Each horizontal seam 518a-c splits its respective fluid bladder 516a-c into two halves in a horizontal zig-zag pattern. Each half of each fluid bladder 516a-c includes fingers, or teeth, that extend between the fingers, or teeth, of the other half. Though the fingers shown in FIG. 7 are triangular, they can also be in any other shape. The design is configured such that the halves are interleaved, allowing each half of each fluid bladder 516a-c to sense position in a linear manner. By separating the fluid bladders 516a-c into interleaved halves, the pressure can be measured independently in each half.

In one example, the fluid bladders 516a-c can include or be in communication with the array of sensors 514 as described in FIG. 6. The pressure in the left half of each fluid bladder 516a-c will increase linearly as a subject moves toward the left side of the back support 500. In a similar manner, the pressure in the right half of each fluid bladder 516a-c will increase linearly as the subject moves toward the right side of the back support 500. The difference in pressure between the halves of the fluid bladders 516a-c can be used to represent the horizontal position of the subject sitting against the back support 500. As was described in reference to FIG. 6, the pressure differential between the left and right halves of the fluid bladders 516a-c is also useful for capturing positional data over time and feeding the results to the control unit 506 to send commands to the pump 508 to inflate or deflate the fluid bladders 502a-c to manipulate the position of the subject against the back support 500.

The seat back supports 500 are portable so that the subject can move it from location to location. For example, a driver for a company that does not driver the same truck all the time can use the seat back support 500 in every vehicle he drives. The seat back support 500 can receive power through a vehicle accessory plug.

In various examples, external network devices, remote controllers and voice controllers may be used to input commands, such as from the subject or a remote system, to control one or more components of the smart seat system. The commands may be transmitted to controller 24 or control unit 15, which can process the command to determine the appropriate component to route the received command.

For example, a subject may input a desired temperature into a remote control, or a control panel wired to the smart seat. The temperature controller in control box 25 may be then configured to increase or decrease the temperature of the smart seat or the fluid in the smart seat's bladders depending on the temperature originally input into the remote control.

In various examples, multiple types of devices may be used to input commands to control the pump 14 and other components of the smart seat, such as a mobile device such as a smart phone or tablet computer running an application. In various examples, remote controls and display 27 can include a display device for displaying an interface to a user and may also include one or more input devices. Input devices may include, but are not limited to, keypads, touch-screen, gesture, motion and voice controls.

Methods of using the smart seat 10 and smart seat support 500 are also disclosed. One method of using a smart seat includes tracking data during use of the smart seat over time and using the historical data to assist the subject.

Figure 8:
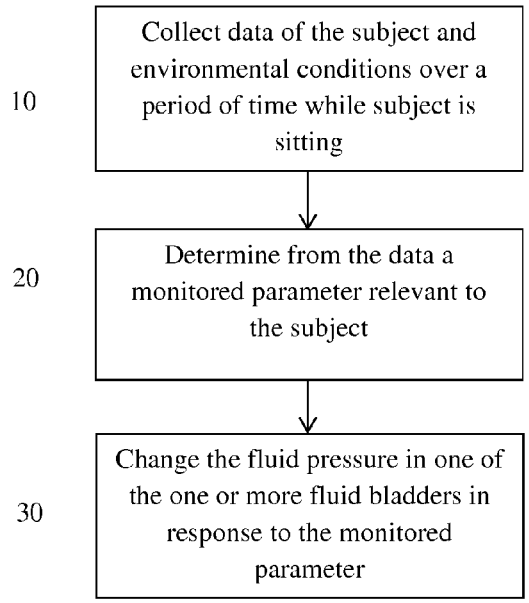
FIG. 8 is a flow diagram of a method of using a smart seat or smart seat support as disclosed herein.

One method of monitoring a subject in a seat is shown in FIG. 8 and comprises in step 10 collecting with a computer data from a smart seat system when a subject is seated in the smart seat system. The smart seat system comprises a first layer of one or more fluid bladders packaged within a seat cushion, a pump in fluid communication with the first layer, the pump operable to increase fluid pressure of each bladder within the first layer and an array of one or more sensors in fluid communication with the first layer and operative to sense pressure and pressure changes within each bladder within the first layer. The data comprises one or more of: absolute pressure of the one or more fluid bladders over time; at least one of a heart rate and a respiration rate of the subject over time based on a first range of pressure changes in at least one of the one or more bladders; length of sitting episodes of the subject in the seat over time; and shifting of the subject in the seat during the sitting episodes based on a second range of pressure changes in the one or more bladders. A monitored parameter relevant to the subject is determined in step 20 from the data and the fluid pressure in one of the one or more fluid bladders is changed in response to the monitored parameter in step 30.

Figure 9:
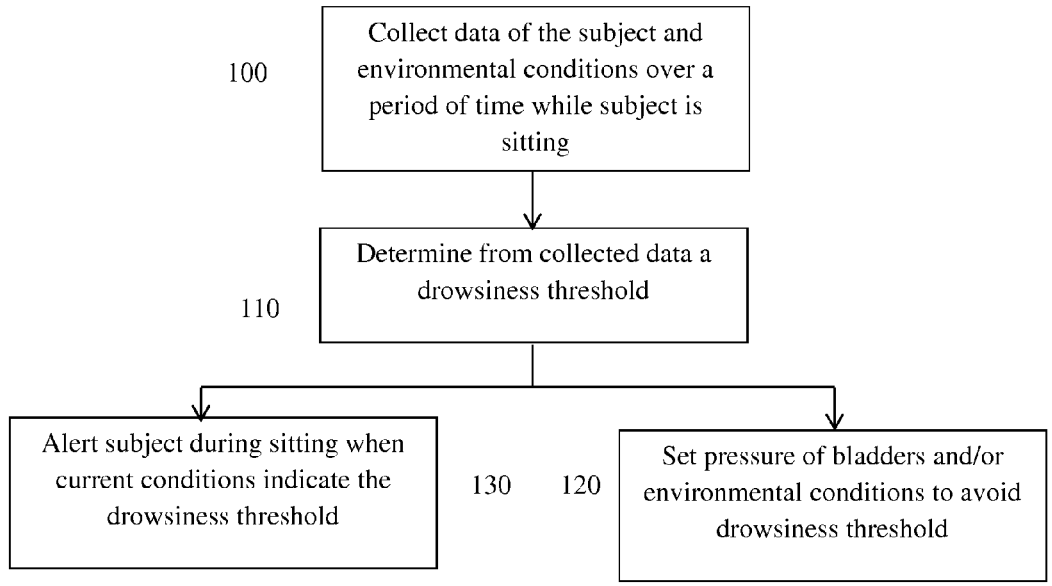
FIG. 9 is a flow diagram of another method of using a smart seat or smart seat support as disclosed herein.

For example, a method of determining a drowsiness threshold or sleepiness factor for a subject can comprise collecting data over a period of use of the smart seat by the subject in step 100 of FIG. 9. The subject may be a driver of an automobile. When the driver is driving the vehicle, particularly for extended periods of time, the smart seat system will monitor and store data. This data can include one or more of the pressure in each bladder in the smart seat, the driver's hear rate and respiratory rate, the temperature of the ambient air in the automobile, the time of day, the period of time between exiting the smart seat, the temperature of the smart seat and the incline of the vehicle seat back. The subject can input data that is also tracked and correlated with the stored data. For example, the subject can alert the system that it is sleepy so that the system correlates the sleepiness with the seat data and atmospheric data collected. This can be as simple as pressing a selection on a screen of the display 27. Over time, with sufficient data, the controller 24 in step 110 can determine a drowsiness threshold, or sleepiness threshold, for the particular driver based on the historical data stored and inputted by the driver. The determination can be performed by the controller 24 or another processor in communication with the database.

The sleepiness threshold can, for example, indicate impending sleep when heart rate is low, when respiratory rate is low, and when movements are infrequent. Over time, the database can accumulate sleepiness thresholds for a variety of conditions (e.g., a lower pressure in one or more fluid bladders, a high pressure in one or more fluid bladders, a cool temperature, and/or a warm temperature).

Based on the determination, a pressure setting can be determined for customizing the environmental conditions (e.g., pressure in the one or more bladders and temperature in the vehicle) to achieve a low sleepiness threshold. The settings can be automatically initiated when the driver is identified in the smart seat, in step 120. Additionally, other settings can be determined and/or modified based on the association. The driver can be identified amount a plurality of drivers by associating a particular driver with his or her vital signs after enough vital sign data has been collected to make the identification. Identifications can be stored in the system by the controller 24, for example.

The sleepiness threshold in combination with the alerting system 29 can be utilized by automobile drivers to assist in preventing the driver from falling asleep. For example, drivers unaccustomed to traveling extended distances, such as driving to a vacation destination, may become drowsy while driving. The sleepiness threshold and alerting system 29 can alert the driver in step 130 that his or her characteristics are indicating that sleepiness is nearing a dangerous level. The sleepiness threshold can also be used for long-haul truck drivers to monitor their vital signs and other characteristics, along with time on the road, so shown compliance with rules and monitor sleepiness patterns.

The alerting system 29 can be incorporated into the display 27 or be a separate unit as illustrated. The alerting system 29 can include an audio component, such as an alarm, or a voice command or warning. The alerting system 29 can display flashing lights or other visual indicators on the display unit 27. The alerting system 29 can communicate with the controller 24 or control unit 15 to change a condition of the smart seat 10 to alert the driver, such as changing the pressure in one or more bladders, changing a temperature of the seat cushion or seat back, or initiating a vibrating component in the vehicle. These alerting mechanisms are examples and are not meant to be limiting.

Another method of using the smart seat 10 and smart seat support 500 can comprise monitoring a subject that sits for extended periods of time at work in an office or other work setting. Data can be tracked and can include one or more of the pressure in each bladder in the smart seat, the subject's heart rate and respiratory rate, the temperature of the ambient air in the office or work space, the time of day, the period of time between exiting the smart seat, the temperature of the smart seat or support and the incline of the seat back. The subject can input data that is also tracked and correlated with the stored data. In data can be used to identify slow parts of the day when the subject's vital signs lag, using such parts of the day to optimize break time or alert the subject to get up and move around. If the smart seat support 500 is used, it can be powered by a computer at the desk of the subject with a USB or charged via an outlet. The data could be sent to a computer of the subject with a USB connection or wirelessly.

Another method of using the smart seat 10 or smart seat support 500 in any situation in which long term sitting occurs includes inflating and deflating the plurality of bladders throughout the sitting period so apply different pressure points on the subject during the sitting period. As one example, the bladders could be inflated/deflated in a pattern that optimizes circulation of the subject's legs over the sitting period without the subject getting up from the sitting position. For example, with reference to FIG. 2, the pressure can be sequentially adjusted over time through the grid of bladders in 28e so that pressure points on the subject changes over a period of time. As another example, the bladders could be inflated/deflated in a pattern that responds to the pressure exerted by the subject on the bladders. For example, with reference to FIG. 3, if the subject is sitting further back in the seat 10, the bladder to the rear of the seat 10 may increase in pressure to provide a firmer support to the subject.

While the embodiments above have been described in connection with what is presently considered to be the most practical example, it is to be understood that the disclosure is not to be limited to these examples but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. A seat monitoring system comprising:
a first layer of one or more fluid bladders packaged within a seat;
a pump in fluid communication with the first layer, the pump operable to increase fluid pressure of each bladder within the first layer;
an array of one or more sensors in fluid communication with the first layer and operative to sense pressure and pressure changes within each bladder within the first layer; and
a controller configured to:
collect pressure data;
determine from the pressure data a monitored parameter relevant to a subject in the seat; and
change an aspect of the seat based on the monitored parameter; and
an array of one or more actuators for controlling the first layer and configured to communicate with the controller and the pump;
wherein the array of one or more actuators and the pump receive commands from the controller based on the monitored parameter to increase or decrease fluid pressure in one or more bladders within the first layer;
wherein the array of one or more actuators is configured to selectively target a region of the first layer to increase or decrease fluid pressure in that region, the region including one or more fluid bladders; and
wherein the monitored parameter is the subject's position, at least one of the one or more fluid bladders comprises interleaved halves and the subject's position is based on a difference in pressure between the interleaved halves.

2. The seat monitoring system of claim 1, wherein the monitored parameter is at least one vital sign including the subject's heart rate and the subject's respiration rate.

3. The seat monitoring system of claim 1, wherein the monitored parameter is the subject's lack of movement, and the controller is configured to send commands to the array of one or more actuators to increase or decrease the fluid pressure in the one or more bladders within the first layer when the lack of movement has elapsed for a threshold time period.

4. The seat monitoring system of claim 1, wherein the monitored parameter is the subject's sleepiness level.

5. The seat monitoring system of claim 1, wherein the control unit communicates with an external device coupled to a display configured to display the monitored parameter.

6. The seat monitoring system of claim 5, wherein the external device comprises a memory configured to store a database of information generated over time including at least one of the pressures within the first layer of fluid bladders and vital signs of the subject.

7. The seat monitoring system of claim 1, wherein the seat is a vehicle driver seat and the control unit communicates with a vehicle system configured to provide an alert to the subject in the vehicle driver seat based on the monitored parameter.

8. The seat monitoring system of claim 1 further comprising:
a temperature sensor, wherein the controller is further configured to receive and store temperature data from the temperature sensor, wherein determining the monitored parameter comprises evaluating data by recording more than one of:
absolute pressure of the one or more fluid bladders over time;
at least one of a heart rate and a respiration rate of the subject over time based on a first range of pressure changes in at least one of the one or more bladders;
length of sitting episodes of the subject in the seat over time; and
shifting of the subject in the seat during the sitting episodes based on a second range of pressure changes in the one or more bladders, and
wherein evaluating the data over the time comprises accessing periods of drowsiness of the subject based on the data.

9. The seat monitoring system of claim 8 further comprising an alerting mechanism configured to receive a signal from the controller, the controller further configured to:
determine a sleepiness threshold from the evaluated data;
determine during monitoring of the subject when current data is approaching the sleepiness threshold; and
send the signal to the alerting mechanism to alert the subject to make a change in at least one of temperature, position, rising from the seat, pressure in at least one of the one or more fluid bladders.

10. The seat monitoring system of claim 9, wherein the seat is a vehicle driver seat.

11. The seat monitoring system of claim 8, wherein the controller is further configured to:
determine a sleepiness threshold from the evaluated data;
determine during monitoring of the subject when current data is approaching the sleepiness threshold; and
send a signal to the alerting mechanism to alert the subject to make a change in at least one of temperature, position, rising from the seat, pressure in at least one of the one or more fluid bladders.

12. The seat monitoring system of claim 1 further comprising:
a second layer of fluid bladders packaged within the seat;
the pump in fluid communication with the second layer, the pump operable to increase fluid pressure of each bladder within the second layer; and
an array of one or more actuators for controlling the second layer and configured to communicate with the controller and the pump;
wherein the array of one or more actuators and the pump receive commands from the controller to increase or decrease fluid pressure in one or more bladders within the second layer based on the monitored parameter.

13. A method of monitoring a subject in a seat comprising:
collecting with a computer data from a smart seat system when a subject is seated in the smart seat system, the smart seat system comprising:
a first layer of one or more fluid bladders packaged within a seat cushion;
a pump in fluid communication with the first layer, the pump operable to increase fluid pressure of each bladder within the first layer; and
an array of one or more sensors in fluid communication with the first layer and operative to sense pressure and pressure changes within each bladder within the first layer;
wherein the data comprises one or more of:
absolute pressure of the one or more fluid bladders over time;
at least one of a heart rate and a respiration rate of the subject over time based on a first range of pressure changes in at least one of the one or more bladders;

length of sitting episodes of the subject in the seat over time; and shifting of the subject in the seat during the sitting episodes based on a second range of pressure changes in the one or more bladders; and determining from the data a monitored parameter relevant to the subject; and changing the fluid pressure in one of the one or more fluid bladders in response to the monitored parameter; and wherein the monitored parameter is the subject's position, at least one of the one or more fluid bladders comprises interleaved halves and the subject's position is based on a difference in pressure between the interleaved halves.

14. The method of claim 13, wherein the smart seat system further comprises a temperature sensor, the method further comprising:

receiving and storing temperature data from the temperature sensor;

evaluating the collected data to accessing periods of drowsiness of the subject based on the collected data.

15. The method of claim 14 wherein the smart seat system further comprises an alerting mechanism, the method further comprising:

determining a sleepiness threshold from the evaluated data;

determining during monitoring of the subject when current data is approaching the sleepiness threshold; and initiating the alerting mechanism to alert the subject to make a change in at least one of temperature, position, rising from the seat, and pressure in at least one of the one or more fluid bladders.

16. A seat monitoring system comprising:

a first layer of one or more fluid bladders packaged within a seat;

a pump in fluid communication with the first layer, the pump operable to increase fluid pressure of each bladder within the first layer;

an array of one or more sensors in fluid communication with the first layer and operative to sense pressure and pressure changes within each bladder within the first layer; and a controller configured to:

collect pressure data;

determine from the pressure data a monitored parameter relevant to a subject in the seat; and change an aspect of the seat based on the monitored parameter;

wherein the monitored parameter is the subject's position, at least one of the one or more fluid bladders comprises interleaved halves and the subject's position is based on a difference in pressure between the interleaved halves.

17. A seat monitoring system comprising:

a first layer of one or more fluid bladders packaged within a seat;

a pump in fluid communication with the first layer, the pump operable to increase fluid pressure of each bladder within the first layer;

an array of one or more sensors in fluid communication with the first layer and operative to sense pressure and pressure changes within each bladder within the first layer; and a controller configured to:

collect pressure data;

determine from the pressure data a monitored parameter relevant to a subject in the seat; and change an aspect of the seat based on the monitored parameter a second layer of fluid bladders packaged within the seat;

the pump in fluid communication with the second layer, the pump operable to increase fluid pressure of each bladder within the second layer; and an array of one or more actuators for controlling the second layer and configured to communicate with the controller and the pump;

wherein the array of one or more actuators and the pump receive commands from the controller to increase or decrease fluid pressure in one or more bladders within the second layer based on the monitored parameter.

* * * * *